(12) United States Patent
Gilbert

(10) Patent No.: US 7,097,634 B2
(45) Date of Patent: Aug. 29, 2006

(54) INJECTION DEVICE PROVIDING AUTOMATIC NEEDLE RETRACTION

(75) Inventor: Scott Gilbert, Menlo Park, CA (US)

(73) Assignee: Alza Corporation, Mountain View, CA (US)

( * ) Notice: Subject to any disclaimer, the term of this patent is extended or adjusted under 35 U.S.C. 154(b) by 463 days.

(21) Appl. No.: 10/632,943

(22) Filed: Jul. 31, 2003

(65) Prior Publication Data

US 2004/0024367 A1 Feb. 5, 2004

Related U.S. Application Data

(60) Provisional application No. 60/400,093, filed on Jul. 31, 2002.

(51) Int. Cl.
*A61M 37/00* (2006.01)
(52) U.S. Cl. .................... 604/150; 604/135; 604/197; 604/110
(58) Field of Classification Search .............. 604/110, 604/131, 134, 135, 181, 187, 194, 197, 198, 604/218, 221, 222, 150
See application file for complete search history.

(56) References Cited

U.S. PATENT DOCUMENTS

| | | | |
|---|---|---|---|
| 4,188,949 A * | 2/1980 | Antoshkiw ............ | 604/191 |
| 4,678,461 A | 7/1987 | Mesa | |
| 5,092,843 A | 3/1992 | Monroe | |
| 5,102,393 A | 4/1992 | Sarnoff | |
| 5,300,030 A | 4/1994 | Crossman | |
| 5,330,430 A | 7/1994 | Sullivan | |
| 5,354,286 A | 10/1994 | Mesa | |
| 5,665,071 A | 9/1997 | Wyrick | |
| 5,695,472 A | 12/1997 | Wyrick | |
| 5,957,897 A * | 9/1999 | Jeffrey ................ | 604/223 |
| 6,149,626 A | 11/2000 | Bachynsky et al. | |
| 6,159,181 A | 12/2000 | Crossman et al. | |
| 6,171,276 B1 | 1/2001 | Lippe et al. | |
| 6,387,078 B1 | 5/2002 | Gillespie, III | |

OTHER PUBLICATIONS

International Search Report from PCT/US03/24113 dated Nov. 6, 2003.

* cited by examiner

*Primary Examiner*—Kevin Sirmons
*Assistant Examiner*—Laura C. Schell
(74) *Attorney, Agent, or Firm*—Angela N. Nwaneri

(57) ABSTRACT

The present invention includes an automatic injection device that reliably provides automatic needle retraction even when manufactured with part and assembly tolerances typical of low-cost and high-volume manufacturing processes. The injector of the present invention includes a body, a syringe cartridge, a drive mechanism, and a bias mechanism. The drive mechanism includes an energy source, a drive member, and a compound plunger with a releasable coupling. Significantly, the compound plunger included in the drive mechanism is designed to ensure needle retraction occurs after the automatic injection device has delivered the desired dose of medicament. Moreover, the design of the compound plunger included in the injector of the present invention can compensate for part and assembly tolerances typical of low-cost, high volume manufacturing processes, enabling the fabrication of a low cost automatic injection device providing reliable automatic needle retraction.

33 Claims, 3 Drawing Sheets

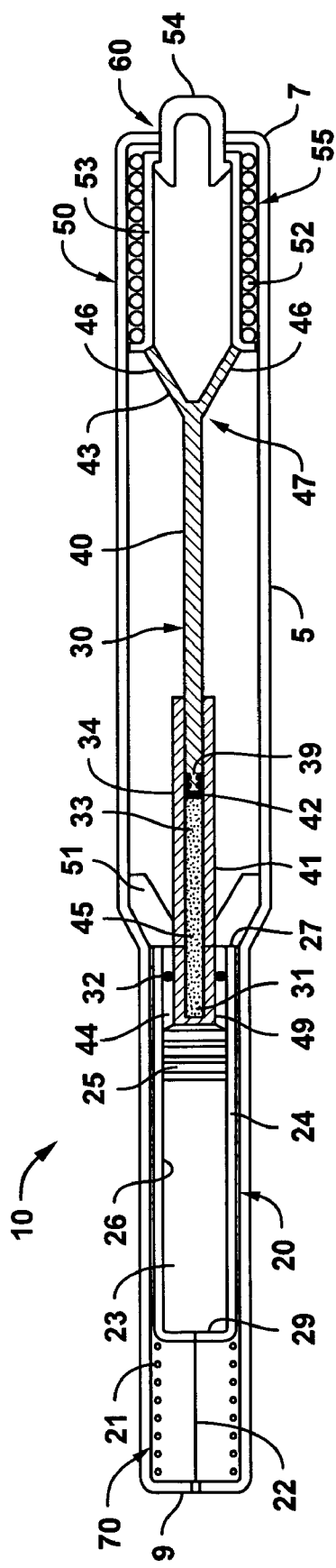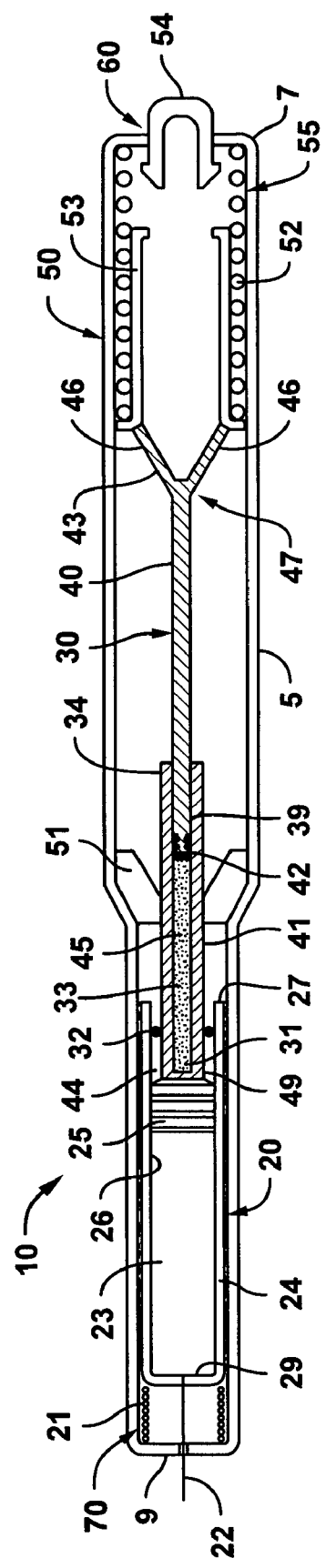
FIG. 1
FIG. 2

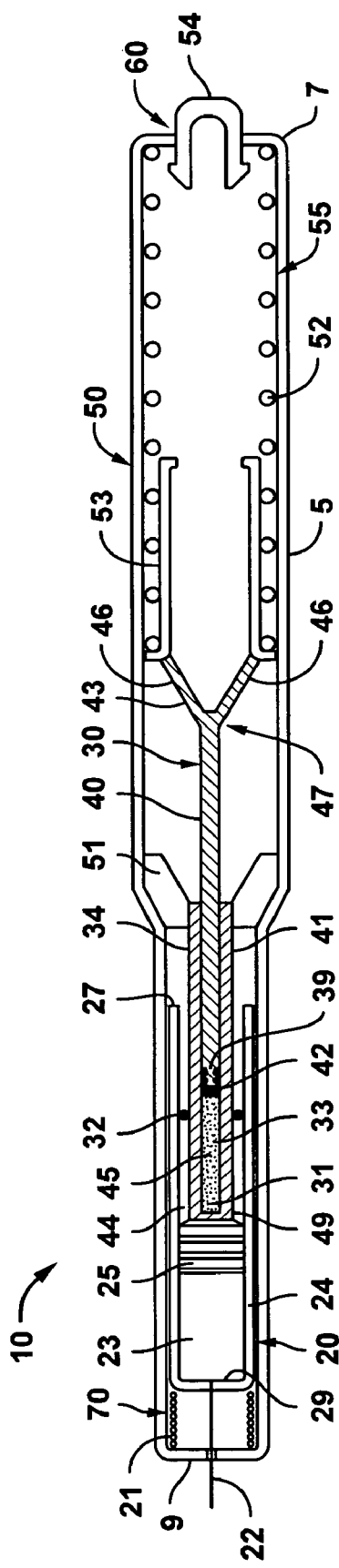
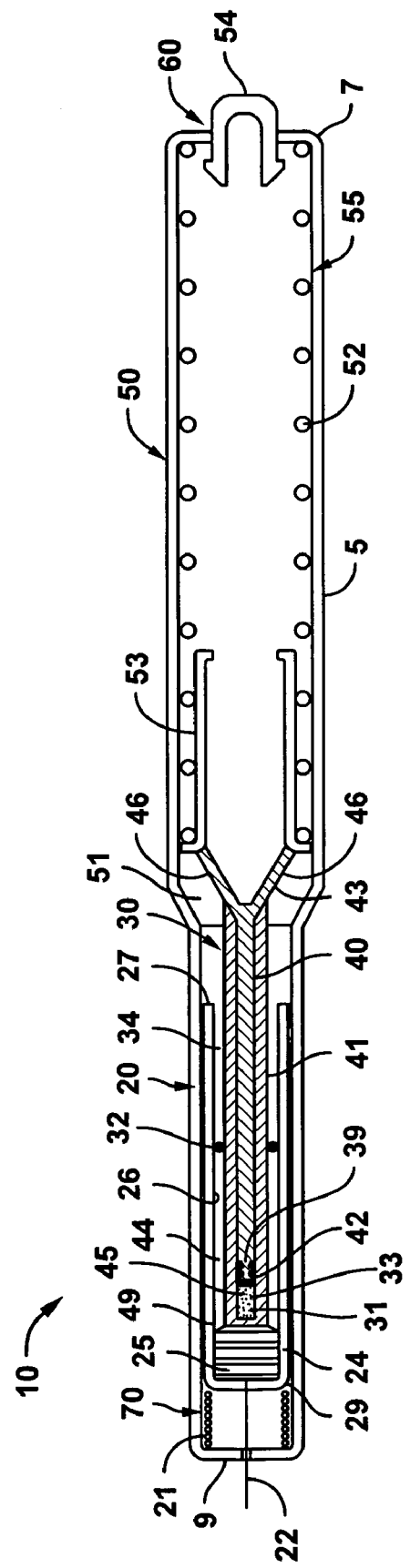
FIG. 3
FIG. 4

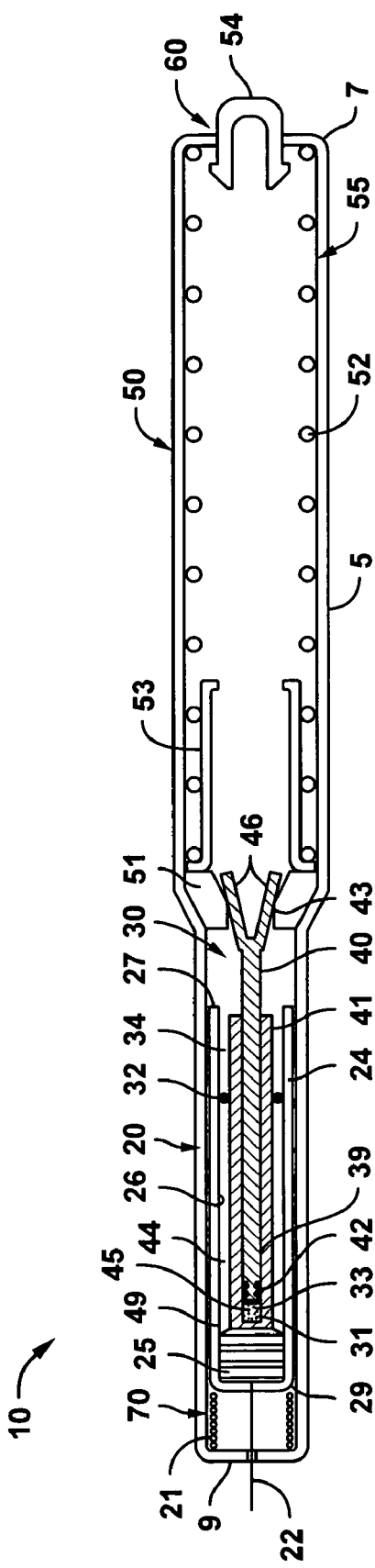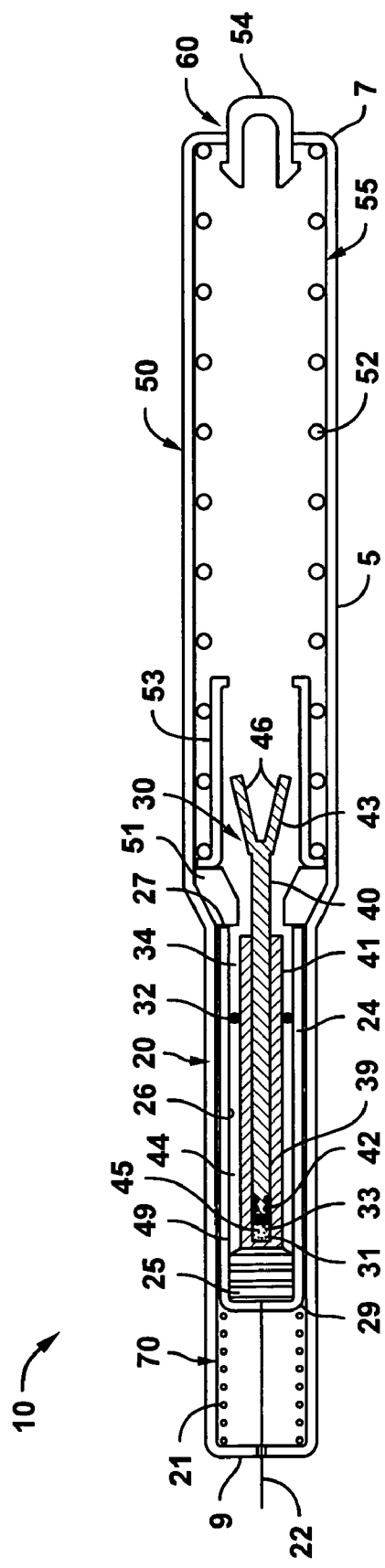

INJECTION DEVICE PROVIDING AUTOMATIC NEEDLE RETRACTION

BACKGROUND

This application claims the benefit of U.S. Provisional Application No. 60/400,093, filed Jul. 31, 2002.

FIELD OF THE INVENTION

The present invention relates to injection devices providing automatic needle insertion, automatic delivery of a desired dose of medicament, and automatic needle retraction from the injection site. Specifically, the present invention relates to an automatic injection device that is suited to low-cost and high-volume manufacturing processes and reliably provides automatic needle insertion and complete delivery of a desired dose of medicament followed by automatic needle retraction from the injection site.

STATE OF THE ART

Injection devices providing automatic needle insertion, automatic injection of a desired medicament, and automatic needle retraction from the injection site are known in the art. Such devices are thought to impart advantages over simple hypodermic syringes. For example, because they may be designed such that the needle included in the injection mechanism is hidden from view before, during, and after an injection, injection devices providing automatic needle insertion and retraction are thought to reduce the anxiety often associated with needled injection devices. Moreover, a device providing both automatic insertion and automatic retraction of the needle used to effect an injection may be designed to shield the needle from contact before and after an injection takes place and thereby reduce the possibility of accidental needle stick injuries. As is exemplified in U.S. Pat. Nos. 6,159,181 ("the '181 patent"), 6,487,732 ("the '732 patent"), and 6,387,078 ("the '078 patent"), the contents of each of which are incorporated herein in their entirety by reference, state of the art automatic injection devices capable of automatic needle retraction generally incorporate a retraction mechanism designed to decouple a needle bearing device, such as a syringe or syringe cartridge, from the drive mechanism used to insert the needle and deliver the medicament from the injection device. Once the needle-bearing device is decoupled from the drive mechanism, a bias member, such as a coil spring, is free to force the needle-bearing device rearwardly within the body of the injection device such that the needle is completely shielded from contact.

Though the '181, '732, and '078 patents succeed in offering injection devices capable of automatic needle insertion, medicament delivery, and needle retraction, the devices taught in the '181, '732, and '078 patents are not without disadvantages. For example, in order to achieve an injection device that provides both complete delivery of medicament and reliable needle retraction using the designs taught in the '181, '732, and '078 patents, various parts included in the injection device must be machined or otherwise fabricated to extremely tight tolerances. The retraction mechanisms taught in the '181, '732, and '078 patents are intended to disengage a plunger acting against the needle-bearing device from the drive mechanism once the plunger has terminated its travel at the end of a drug delivery stroke. Termination of plunger travel and decoupling of the plunger from the drive mechanism must occur simultaneously if both complete delivery of medicament and automatic needle retraction are to be accomplished. However, the injector designs taught in the '181, '732, and '078 patents include no feedback mechanism to ensure that the retraction mechanism decouples the plunger from the drive mechanism precisely as the plunger reaches the end of its travel. Instead, only mechanical position is used to activate the retraction mechanism at the point where it is expected that plunger travel will cease. The precision of the timing of the termination of plunger travel and decoupling of the plunger from the drive mechanism relies entirely on the accuracy of the part and assembly dimensions of the injection device. Therefore, the variability of the part and assembly dimensions, that is, the tolerances, play a critical role in the proper function of the injection devices taught in the '181, '732, and '078 patents.

It is well known that in multipart assemblies, such as an automatic injection device, the tolerances of the various parts accumulate or "stack-up" to give a sum deviation from the design specification. In injection devices designed according to the '181, '732, and '078 patents, a tolerance stack-up of as little as 0.005" away from a specified value may cause early or late actuation of the retraction mechanism. If the retraction mechanism actuates too early, the plunger will be decoupled from the drive mechanism before the plunger has terminated its travel within the needle bearing devices, leaving an amount of medicament undelivered. Conversely, if a tolerance stack-up causes late actuation of the retraction mechanism, the plunger will not be fully decoupled from the drive mechanism as the plunger ceases travel, and the needle will fail to automatically retract. Therefore, to ensure complete dosing and reliable needle retraction using an injection device designed according to any of the '181, '732, and '078 patents, the various parts of the injection device must be machined or otherwise fabricated to tolerances that are typically not practical in a low-cost, high-volume production context. Moreover, the tight tolerances required for reliable operation of the devices taught in the '181, '732, and '078 patents would prevent the use of commercially available standardized syringes, such as a Becton Dickenson Hypak™ syringe, which are generally not designed with such tolerances in mind. It would be an improvement in the art, therefore, to provide an automatic injection device that can be manufactured in high volumes at low costs, while reliably effecting complete delivery of a desired dose of medicament followed by automatic needle retraction.

SUMMARY OF THE INVENTION

The present invention includes an automatic injection device that reliably provides automatic needle retraction even when manufactured with part and assembly tolerances typical of low-cost and high-volume manufacturing processes. The injector of the present invention includes a body, a syringe cartridge, a drive mechanism, and a bias mechanism. The syringe cartridge includes a syringe capable of containing a desired medicament and an associated needle to effect injection. The drive mechanism includes an energy source, a drive member, and a compound plunger with a releasable coupling. The energy source included in the drive mechanism exerts a force against the drive member and such force is transferred to the syringe cartridge through the compound plunger, which is releasably coupled to the drive member. The transfer of force from the energy source through the drive member and compound plunger to the syringe cartridge displaces the syringe cartridge and associated needle to an extended position, effecting needle insertion followed by delivery of a medicament contained within the syringe. After delivery of the medicament is complete, the releasable coupling of the compound plunger is actuated and the compound plunger is decoupled from the drive member of the drive mechanism, freeing the bias mechanism to return the syringe cartridge and associated needle to a retracted position within the syringe body. The compound plunger included in the drive mechanism is designed to ensure that retraction of the syringe cartridge occurs after delivery of the desired dose of medicament. Moreover, the design of the compound plunger included in the injector of the present invention can compensate for part and assembly tolerances typical of low-cost, high volume manufacturing processes, enabling the fabrication of a low cost automatic injection device providing reliable automatic needle retraction.

BRIEF DESCRIPTION OF THE DRAWINGS

FIG. 1 illustrates a schematic cross-sectional view of an embodiment of the injector of the present invention in a ready but unactivated state.

FIG. 2 illustrates the injector of FIG. 1 following activation.

FIG. 3 illustrates the injector of FIG. 1 following activation and partial completion of the drug delivery stroke.

FIG. 4 illustrates the injector of FIG. 1 at the completion of the drug delivery stroke but prior to initiation of needle retraction.

FIG. 5 illustrates the actuation of the releasable coupling included in the injector illustrated in FIG. 1.

FIG. 6 illustrates the injector of FIG. 1 following completion of the drug delivery stroke and actuation of the releasable coupling.

DETAILED DESCRIPTION OF THE INVENTION

An embodiment of an injector according to the present invention is successively illustrated in FIG. 1 through FIG. 6. As can be appreciated by reference to the figures, an injector 10 according to the present invention includes a body 5 housing a syringe cartridge 20, a trigger mechanism 60, a drive mechanism 50 that utilizes a compound plunger 30, and a bias mechanism 70 for retaining the syringe cartridge 20 within the body 5 of the injector 10. The body 5 of an injector 10 of the present invention includes a proximal end 7 and a distal end 9. Though the figures included herein illustrate a body 5 that is generally cylindrical with a wider diameter at the proximal end 7 tapering to a narrower diameter at the distal end 9, the body 5 of the injector 10 of the present invention may be formed according to any size or shape capable of housing or supporting the syringe cartridge 20, the drive mechanism 50, the compound plunger 30, and the trigger mechanism 60 included in the injector 10 of the present invention. Additionally, the body 5 of the injector 10 of the present invention may be formed of one or more associable parts, as desired.

The syringe cartridge 20 included in the injector 10 of the present invention includes a syringe 24 having a proximal end 27 and a distal end 29. The syringe 24 of the syringe cartridge 20 is capable of containing a desired medicament 23 and is configured to receive or bear a needle 22. The syringe cartridge 20 also includes a piston 25 that is sealingly engaged with the walls 26 of the syringe 24 and is movable within the syringe 24 to effect expulsion of a medicament 23 through the needle 22. Though the piston 25 illustrated in FIG. 1 through FIG. 6 is not affixed to or part of the compound plunger 30, where desired, the compound plunger 30 can be configured such that the piston 25 is affixed to or integral with the compound plunger 30.

As can be appreciated by reference to FIG. 1 through FIG. 6, the syringe cartridge 20 is positioned within the body 5 of the injector 10 in a manner that allows back and forth movement of the syringe cartridge 20 within the body 5. The syringe cartridge 20 may be designed to suit virtually any application and may include any reservoir, needle, or piston suited for the injection of medicament. For example, the syringe cartridge 20 may be specifically designed for operation with an injector having a particular configuration or application, or, alternatively, the syringe cartridge 20 of the injector of the present invention may be embodied by one of many commercially available, standardized syringes, such as a Becton Dickenson Hypack™ syringe.

The bias mechanism 70 included in the injector 10 of the present invention exerts a bias force sufficient to maintain the syringe cartridge 20 within the body 5 of the injector 10 until the drive mechanism 50 of the injector 10 is activated. Any device or mechanism capable of exerting sufficient bias force against the syringe cartridge 20 may be used as the bias mechanism 70. As is shown in FIG. 1 through FIG. 6, the bias mechanism 70 may simply include a coil spring 21 positioned between the syringe cartridge 20 and the distal end 9 of the body 5 of the injector 10 such that the coil spring 21 biases the syringe cartridge 20 in a retracted position. Alternatively, the bias mechanism 70 may include an elastic bumper formed of a natural or synthetic material, or the bias mechanism 70 may include a plurality of coil springs or a plurality of elastic bumpers working to bias the syringe cartridge 20 in a retracted position. Again, however, the bias mechanism 70 is not limited to the embodiments described or illustrated herein and may include any device or mechanism capable of exerting sufficient bias force against the syringe cartridge 20.

The drive mechanism 50 of the injector 10 of the present invention includes an energy source 55, a drive member 53, and a compound plunger 30. The energy source 55 included in the drive mechanism 50 of the injector 10 of the present invention may include any material, mechanism or device capable of generating a force sufficient to motivate the drive member 53 distally through the body 5 of the injector 10. As the energy source 55 motivates the drive member 53 distally, the drive member 53 drives the compound plunger 30 against the piston 25 of the syringe cartridge 20, displacing the syringe cartridge 20 from a retracted position to an extended position and causing the medicament 23 contained within the syringe cartridge 20 to be expelled through the needle 22 associated with the syringe 24. As the syringe cartridge 20 is displaced from a retracted position to an extended position, the needle 22 associated with the syringe cartridge 20 extends from the body 5 of the injector 10 with sufficient force to penetrate the tissue of a desired subject. The force exerted by the energy source 55 of the injector 10 of the present invention, therefore, is of sufficient magnitude to overcome the bias mechanism 70, to insert the needle 22 into the tissue of the subject, and to expel a desired amount of medicament from the syringe 24 through the needle 22 and into the subject. Though any energy source 55 capable of exerting a suitable force may be used in the drive mechanism 50 of the present invention, for reasons of simplicity and cost, the energy source 55 of the drive mechanism 50 of the injector 10 of the present invention is preferably a coil spring 52.

The drive member 53 and compound plunger 30 included in the drive mechanism 50 are configured to allow the compound plunger 30 to decouple from the drive member 53 after a desired dose of medicament 23 has been expelled from the syringe 24. Decoupling of the compound plunger 30 from the drive member 53 frees the compound plunger 30 from the force exerted by the energy source 55 of the drive mechanism 50 and allows the bias mechanism 70 to drive the syringe cartridge 20 and the associated needle 22 back from an extended position to a retracted position. Though a suitable configuration for the drive member 53 included in the injector 10 of the present invention is illustrated in accompanying figures, the drive member 53 is not so limited. The drive member 53 included in the drive mechanism 50 of injector 10 of the present invention may be designed according to any configuration that allows the force exerted by the energy source 55 to be transferred to the compound plunger 30 and facilitates decoupling of the compound plunger 30 from drive member 53 after a desired dose of medicament 23 has been delivered.

The trigger mechanism 60 included in the injector of the present invention may include any mechanism capable of causing the energy source 55 included in the drive mechanism 50 to exert a motivating force against the drive member 53. For example, where the energy source 55 of the drive mechanism 50 includes a coil spring 52, the trigger mechanism 60 of the injector 10 of the present invention may include an actuation button 54 configured to retain the drive member 53 in a ready state, wherein the drive member 53 is in a retracted position and the coil spring 52 is compressed (shown in FIG. 1). In such an example, manipulation of the actuation button 54, such as by application of a depressive force, frees the drive member 53 from the retracted position and allows the coil spring 52 to expand, motivating the drive member 53 distally through the body 5 of the injector 10 with a desired amount of force (shown in FIG. 2 through FIG. 5). Trigger mechanisms suitable for use in the injector 10 of the present invention are disclosed in the '181, '732, and '078 patents and in U.S. Patents Nos. 6,149,626, 5,957,897, 5,695,472, 5,665,071, 5,354,286, 5,300,030, 5,102,393, 5,092,843, 4,678,461, and 3,797,489, and the contents of each of these patents are incorporated in their entirety herein by reference.

It is the compound plunger 30 included in the drive mechanism 50 of the injector 10 of the present invention that enhances the reliability with which the injector 10 of the present invention provides complete medicament dosing and automatic needle retraction, while allowing the parts of the injector 10 to be fabricated and assembled at tolerances suited to low-cost, high-volume manufacturing processes. The compound plunger 30 provided in the drive mechanism 50 of the injector 10 of the present invention includes an inner plunger 40 and an outer plunger 41, with the inner plunger 40 being movable within a first reservoir 33 formed by the outer plunger 41. The distal end 39 of the inner plunger 40 includes a sealing member, such as a piston 42, that is sealingly engaged with walls 34 of the first reservoir 33. The first reservoir 33 formed by the outer plunger 41 contains a hydraulic fluid 45, and the hydraulic fluid 45 contained within the first reservoir 33 is in fluid communication with a second reservoir 44 via a hydraulic orifice 31, which extends through a wall 34 of the outer plunger 41. The second reservoir 44 is formed between the syringe 24 and the external surface of the outer plunger 41. The proximal boundary of the second reservoir 44 is formed by a sealing member 32, such as an elastomeric 0-ring, positioned around the outer plunger 41 and forming a slidable seal between the outer plunger 41 and the syringe 24 of the syringe cartridge 20, and the distal boundary of the second reservoir 44 is defined by the piston 25 that is displaced within the syringe 24 to effect expulsion of the medicament 23.

The inner plunger 40 included in the compound plunger 30 of the drive mechanism 50 can include a decoupling mechanism. As is shown in FIG. 1–FIG. 6, a releasable coupling 43 may be formed integrally with the inner plunger 40. Alternatively, the a releasable coupling 43 can be positioned on or around the inner plunger 40, affixed to the inner plunger 40, or otherwise operatively associated with the inner plunger 40. The releasable coupling 43 illustrated in FIG. 1–FIG. 6 interfaces with the drive member 53 in a manner that allows the drive member 53 to transfer the force exerted by the energy source 55 to the inner plunger 40. However, the releasable coupling 43 is designed to facilitate decoupling or release of the inner plunger 40 from the drive member 53 after the syringe piston 25 has reached the distal end 29 of the syringe 24 and the outer plunger 41 has ceased travel.

Various mechanisms for forming a releasable coupling that may be used in an injection device of the present invention are taught in the '181, '732, and '078 patents, the contents of which incorporated in their entirety herein by reference. For example, a releasable coupling 43 may be positioned near or at the proximal end 47 of the inner plunger 40 and may be formed by two or more deflectable arms 46 formed integrally with the inner plunger 40. Were such a configuration used, a decoupling ring 51 may be provided to actuate the releasable coupling 43 by deflecting the two or more deflectable arms 46 as the inner plunger 40 continues to travel through the first reservoir 33 after delivery of the medicament 23 is complete. Actuation of the releasable coupling 43 illustrated in the accompanying figures is complete once the deflectable arms 46 are deflected to such an extent that the coupling between the drive member 53 and the inner plunger 40 can no longer be maintained.

The hydraulic fluid 45 included in the first reservoir 33 may be any suitable hydraulic fluid. For example, hydraulic fluids useful in the compound plunger 30 included in the injector 10 of the present invention include water, silicon medical fluid, glycerin, and similar hydraulic fluids. The hydraulic fluid 45 included in the first reservoir 33 is preferably a substantially non-compressible fluid. Regardless of the specific fluid used, the hydraulic fluid 45 included in the first reservoir 33 of the compound plunger 30 should be of sufficient viscosity and the hydraulic orifice 31 of such a size that capillary action does not cause the hydraulic fluid 45 to wick through the hydraulic orifice 31. Instead the hydraulic fluid 45 should remain within the first reservoir 33 by surface tension until it is forcibly expelled into the second reservoir 44 through the hydraulic orifice 31 by a force exerted against hydraulic fluid 45 by the inner plunger 40. In order to minimize the air entrained in the second reservoir 44, the sealing member 32 is initially positioned about the outer plunger 41 close to and at the proximal side of the hydraulic orifice 31. Preferably, the sealing member 32 remains in place by tension alone such that it is free to slide or roll as the outer plunger 41 moves relative to the syringe 24 as the medicament 23 is being injected. Thus, as the hydraulic fluid 45 is expelled from the first reservoir 33 into the second reservoir 44, the sealing member 32 preferably slides or rolls about the outer plunger 41 and, thereby, automatically increases the volume of the second reservoir 44 to accept the incoming hydraulic fluid 45.

The distal end 49 of the outer plunger 41 is positioned against or near the piston 25 positioned within the syringe 24 of the syringe cartridge 20. Alternatively, the piston 25 may be affixed to or integral with the distal end 49 of the outer plunger 41. Upon activation of the drive mechanism 50 (shown in FIG. 2), the force generated by the energy source 55 of the drive mechanism 50 is applied to the compound plunger 30 through the drive member 53 and the releasable coupling 43 included on the inner plunger 40. The force applied to the inner plunger 40 is applied to the outer plunger 41 through the hydraulic fluid 45 included in the first reservoir 33, and the outer plunger 41, in turn, acts against the piston 25 of the syringe cartridge 20, causing the syringe cartridge 20 to advance against the bias mechanism 70 such that the needle 22 is extended from within the body 5 of the injector 10. Due to the rate at which the force exerted by the energy source 55 is applied upon activation of the drive mechanism 50, the hydraulic fluid 45 included in the first reservoir 33 initially acts essentially as a solid, even though force is being applied to it through the inner plunger 40 and associated piston 42. Therefore, as the syringe cartridge 20 and associated needle 22 are displaced from a retracted position to an extended position within the body 5 of the injector 10, hydraulic fluid 45 does not immediately flow out of the first reservoir 33.

Once the syringe cartridge 20 reaches the end of its travel within the body 5 of the injector 10 and the needle 22 is fully extended, the energy source 55 of the drive mechanism 50 continues to act against the inner plunger 40 through the drive member 53. The inner plunger 40, therefore, continues to transfer the force exerted by the energy source 55 to the outer plunger 41 through the hydraulic fluid 45 contained within the first reservoir 33. The continued application of force through the hydraulic fluid 45 causes the hydraulic fluid 45 to begin to flow out of the first reservoir 33 and into the second reservoir 44 through the hydraulic orifice 31. The continued application of force to the outer plunger 41 also causes the outer plunger 41 to motivate the piston 25 of the syringe cartridge 20 distally within the syringe 24 such that medicament 23 is expelled from the syringe 24 through the needle 22. FIG. 3 illustrates an injector according to the present invention after roughly 60% of the medicament 23 has been dispensed from the syringe 24 and about 50% of the hydraulic fluid 45 has been transferred from the first reservoir 33 to the second reservoir 44. Notably, the force exerted by the energy source 55 of the drive mechanism 50 is not significantly, if at all, diminished as it is transferred through the hydraulic fluid 45 to the outer plunger 41, even as the hydraulic fluid 45 is expelled from the first reservoir 33 into the second reservoir 44.

Delivery of the medicament is completed as the outer plunger 41 drives the piston 25 into the distal end 29 of the syringe 24 (shown in FIG. 4). As the piston 25 reaches the distal end 29 of the syringe 24, distal travel of both the piston 25 and the outer plunger 41 terminates. However, as can be appreciated by reference to FIG. 4, the dimension of the hydraulic orifice 31 as well as the type and volume of hydraulic fluid included in the first reservoir 33 are chosen such that, even after delivery of the medicament 23 is complete, an amount of hydraulic fluid 45 remains within the first reservoir 33 and the releasable coupling 43 included on the inner plunger 40 remains to be actuated. The design of the compound plunger 30 included in the injector 10 of the present invention, therefore, works to ensure that the syringe cartridge 20 and associated needle 22 are retracted only after delivery of the desired dose of medicament 23 is complete.

After delivery of the medicament 23 is complete, the energy source 55 included in the drive mechanism 50 continues to exert a force against the inner plunger 40 through the drive member 53. As is shown in FIG. 5, the force exerted by the energy source 55 causes the inner plunger 40 to continue its travel within the first reservoir 33, resulting in the continued expulsion of hydraulic fluid 45 from the first reservoir 33 into the second reservoir 44. The continued travel of the inner plunger 40 allows actuation of the releasable coupling 43 of the inner plunger 40, resulting in the decoupling of the compound plunger 30 from the drive member 53 of the drive mechanism 50. As the compound plunger 30 is decoupled from the drive member 53, the force exerted by the energy source 55 of the drive mechanism 50 no longer acts against the compound plunger 30, and the bias mechanism 70 is free to once again displace the syringe cartridge 20 and associated needle 22 into a retracted position within the body 5 of the injector 10.

FIG. 6 illustrates an embodiment of the injector of the present invention after the medicament 23 has been delivered, the releasable coupling 43 has actuated, and the needle 22 and syringe 24 are fully retracted. As can be seen in FIG. 6, even after full retraction, an amount of hydraulic fluid 45 may remain within the first reservoir 33. An overage of hydraulic fluid 45 included in the first reservoir 33 is used to effectively compensate for potential part or assembly tolerances that may delay actuation of the releasable coupling 43.

Where part or assembly tolerances delay the actuation of the releasable coupling 43 and the first reservoir 33 does not include a compensatory overage of hydraulic fluid 45, the inner plunger 40 may reach the distal end 49 of the first reservoir 33 before the releasable coupling 43 has actuated. After the inner plunger 40 reaches the distal end 49 of the first reservoir 33, the drive mechanism 50 and the compound plunger 30 will remain static, and unless the releasable coupling 43 has actuated at or before the point at which these mechanisms become static, the syringe cartridge 20 and associated needle 22 will fail to retract. Including an overage of hydraulic fluid 45 within the first reservoir 33 allows the inner plunger 40 to continue distal movement within the first reservoir 33 until the releasable coupling 43 has actuated, even when part or assembly tolerances delay actuation of the releasable coupling 43 and require that the inner plunger 40 travel a greater distance than anticipated to actuate the releasable coupling 43. Once the processes used to manufacture and assemble the injector 10 of the present invention are known, the tolerances provided by the processes can be determined, and the first reservoir 33 can be provided with an overage of hydraulic fluid 45 that allows actuation of the releasable coupling 43, even if the worst tolerance stack-up is realized. The compound plunger 30 of the injector 10 of the present invention, therefore, allows the low-cost mass production of an automatic injection device that reliably provides automatic needle retraction only after the desired dose of medicament has been delivered.

What is claimed:

1. An injection device comprising a syringe cartridge including a needle for delivery of a medicament, a trigger mechanism, a drive mechanism and a bias mechanism,
   wherein the injection device is configured to provide automatic injection of a desired dose of the medicament followed by automatic retraction of the needle associated with the syringe cartridge and the drive mechanism includes a compound plunger,
   wherein the compound plunger comprises an outer plunger forming a first reservoir, a hydraulic fluid contained within the first reservoir, a hydraulic orifice, and an inner plunger positioned at least partially within the outer plunger, the inner plunger being positioned and configured such that, as the drive mechanism operates, the inner plunger acts against the hydraulic fluid and the hydraulic fluid is expelled from the first reservoir through the hydraulic orifice, wherein the injection device further comprises a second reservoir configured to contain the hydraulic fluid expelled from the first reservoir, wherein the second reservoir is at least partially formed by a sealing member included on an outer surface of the outer plunger.

2. The injection device of claim 1, wherein a proximal boundary of the second reservoir is formed by the sealing member included on an outer surface of the outer plunger and a distal boundary of the second reservoir is formed by a piston positioned within the syringe cartridge.

3. The injection device of claim 1, wherein the sealing member included on an outer surface of the outer plunger and a piston positioned within the syringe cartridge form two walls of the second reservoir and the sealing member is disposed around the outer surface of the outer plunger such that the sealing member forms a slidable seal.

4. The injection device of claim 1, wherein the sealing member included on an outer surface of the outer plunger forms a proximal wall of the second reservoir and a piston positioned within the syringe cartridge forms a distal wall of the second reservoir and the sealing member is disposed around the outer surface of the outer plunger such that the sealing member forms a slidable seal and the sealing member is slidable relative to the outer plunger.

5. The injection device of claim 1, wherein the drive mechanism comprises a spring.

6. The injection device of claim 1, wherein the bias mechanism comprises a spring.

7. The injection device of claim 1, wherein the inner plunger further comprises a decoupling mechanism formed integrally therewith.

8. The injection device of claim 1, wherein the inner plunger includes a decoupling mechanism operatively associated therewith.

9. The injection device of claim 1, wherein the inner plunger includes a distal end and a sealing member near the distal end.

10. The injection device of claim 1, wherein the inner plunger includes a distal end and a piston near the distal end.

11. An injection device comprising:
a body incorporating a syringe cartridge, the syringe cartridge containing a medicament to be injected, including a needle through which the medicament can be injected, and being positioned within the body such that the syringe cartridge can be displaced back and forth within the body;
a bias mechanism configured to exert a first force against the syringe cartridge, which first force works to maintain the syringe cartridge in a retracted position within the syringe body;
a drive mechanism comprising an energy source, a drive member, a compound plunger, and a decoupling mechanism, wherein the compound plunger includes an outer plunger forming a first reservoir and, a hydraulic fluid contained within the first reservoir, a hydraulic orifice, and an inner plunger positioned at least partially within the outer plunger; and
a second reservoir configured to contain the hydraulic fluid expelled from the first reservoir, the second reservoir being partially formed between an outer surface of the outer plunger and the syringe cartridge,
wherein the drive mechanism is configured such that, upon actuation, the energy source, drive member, compound plunger, and decoupling mechanism function together to effect automatic extension of the needle of the syringe cartridge from the body of the injection device, automatic delivery of a desired dose of the medicament from the syringe cartridge, and automatic retraction of the needle after delivery of the desired dose of the medicament.

12. The injection device of claim 11, wherein a proximal boundary of the second reservoir is formed by a sealing member included on an outer surface of the outer plunger.

13. The injection device of claim 11, wherein a proximal boundary of reservoir is formed by a sealing member included on an outer surface of the outer plunger and a distal boundary of the second reservoir is formed by a piston positioned within the syringe cartridge.

14. The injection device of claim 11, wherein a proximal boundary of the second reservoir is formed by a sealing member included on an outer surface of the outer plunger and the sealing member is provided on the outer surface of the outer plunger in a manner that the sealing member provides a slidable seal.

15. The injection device of claim 11, wherein a sealing member included on an outer surface of the plunger forms a proximal wall of the second reservoir and a piston positioned within the syringe cartridge forms a distal wall of the second reservoir and the sealing member is disposed around the outer surface of the outer plunger such that the sealing member forms a seal that is slidable relative to the outer plunger such that the sealing member forms a seal that is slidable relative to the outer plunger and to the syringe cartridge.

16. The injection device of claim 11, wherein the energy source of the drive mechanism comprises a spring.

17. The injection device of claim 11, wherein the bias mechanism comprises a spring.

18. The injection device of claim 11, wherein the inner plunger further comprises a decoupling mechanism formed integrally therewith.

19. The injection device of claim 11, wherein the inner plunger includes a decoupling mechanism operatively associated therewith.

20. The injection device of claim 11, wherein the inner plunger includes a distal end and a sealing member near the distal end.

21. The injection device of claim 11, wherein the inner plunger includes a distal end and a piston near the distal end.

22. An injection device comprising:
a body incorporating a syringe cartridge, the syringe cartridge containing a medicament to be injected, including a needle through which the medicament can be injected, and being positioned within the body such that the syringe cartridge can be displaced back and forth within the body;
a bias mechanism configured to exert a first force against the syringe cartridge, which first force works to maintain the syringe cartridge in a retracted position within the syringe body;
a drive mechanism comprising an energy source, a drive member, a compound plunger, and a decoupling mechanism, wherein the compound plunger includes an outer plunger forming a first reservoir, a hydraulic fluid contained within the first reservoir, a hydraulic orifice sized to prevent escape of the hydraulic fluid from the first reservoir by capillary action, and an inner plunger positioned at least partially within the outer plunger, the drive mechanism being configured such that, upon actuation, the energy source, drive member, compound plunger, and decoupling mechanism function together to effect automatic extension of the needle of the syringe cartridge from the body of the injection device, automatic delivery of a desired dose of the medicament from the syringe cartridge, and automatic retraction of the needle after delivery of the desired dose of the medicament; and a second reservoir configured to contain the hydraulic fluid expelled from the first reservoir, the second reservoir being partially formed between an outer surface of the outer plunger and the syringe cartridge.

23. The injection device of claim 22, wherein a proximal boundary of the second reservoir is formed by a sealing member included on an outer surface of the outer plunger.

24. The injection device of claim 22, wherein a proximal boundary of the second reservoir is formed by a sealing member included on an outer surface of the outer plunger and a distal boundary of the second reservoir is formed by a piston positioned within the syringe cartridge.

25. The injection device of claim 22, wherein a proximal boundary of the second reservoir is formed by a sealing member included on an outer surface of the outer plunger and the sealing member is provided on the outer surface of the outer plunger in a manner that the sealing member provides a slidable seal.

26. The injection device of claim 22, wherein a sealing member included on an outer surface of the outer plunger forms a proximal wall of the second reservoir and a piston positioned within the syringe cartridge forms a distal wall of the second reservoir and the sealing member is disposed around the outer surface of the outer plunger such that the sealing member forms a seal that is slidable relative to the outer plunger and to the syringe cartridge.

27. The injection device of claim 22, wherein the energy source of the drive mechanism comprises a spring.

28. The injection device of claim 22, wherein the bias mechanism comprises a spring.

29. The injection device of claim 22, wherein the inner plunger further comprises a decoupling mechanism formed integrally therewith.

30. The injection device of claim 22, wherein the inner plunger includes a decoupling mechanism operatively associated therewith.

31. The injection device of claim 22, wherein the inner plunger includes a distal end and a sealing member near the distal end.

32. The injection device of claim 22, wherein the inner plunger includes a distal end and a piston near the distal end.

33. An injection device comprising:

a body incorporating a syringe cartridge, the syringe cartridge containing a medicament to be injected, including a needle through which the medicament can be injected, and being positioned within the body such that the syringe cartridge can be displaced back and forth within the body;

a bias mechanism configured to exert a first force against the syringe cartridge, which first force works to maintain the syringe cartridge in a retracted position within the syringe body;

a drive mechanism comprising an energy source, a drive member, a compound plunger, and a decoupling mechanism, wherein the compound plunger includes an outer plunger forming a first reservoir, a hydraulic fluid contained within the first reservoir, a hydraulic orifice sized to prevent escape of the hydraulic fluid from the first reservoir by capillary action, and an inner plunger positioned at least partially within the outer plunger, the inner plunger being positioned and configured such that, as the drive mechanism operates, the inner plunger acts against the hydraulic fluid and the hydraulic fluid is expelled from the first reservoir through the hydraulic orifice; and a second reservoir configured to contain the hydraulic fluid expelled from the first reservoir, the second reservoir being formed between an outer surface of the outer plunger, an inner surface of the syringe cartridge, a sealing member included on an outer surface of the outer plunger, and a piston positioned within the syringe cartridge, wherein the sealing member is disposed around the outer surface of the outer plunger such that the sealing member forms a seal that is slidable relative to the outer plunger and to the syringe cartridge.

* * * * *